US00PP34980P2

(12) United States Plant Patent
van Laere et al.

(10) Patent No.: US PP34,980 P2
(45) Date of Patent: Feb. 14, 2023

(54) ***VIBURNUM* PLANT NAMED 'ILVOGAMI'**

(50) Latin Name: *Viburnum plicatum*
Varietal Denomination: 'ILVOGAMI'

(71) Applicant: Spring Meadow Nursery Inc., Grand Haven, MI (US)

(72) Inventors: Katrijn van Laere, Melle (BE); Johan van Huylenbroeck, Melle (BE)

( * ) Notice: Subject to any disclaimer, the term of this patent is extended or adjusted under 35 U.S.C. 154(b) by 0 days.

(21) Appl. No.: 17/726,832

(22) Filed: Apr. 22, 2022

(51) Int. Cl.
*A01H 5/00* (2018.01)
*A01H 6/00* (2018.01)

(52) U.S. Cl.
USPC ..... Plt./226

(58) Field of Classification Search
USPC ..... Plt./226
See application file for complete search history.

(56) References Cited

PUBLICATIONS

CPVO—Register website citation for ILVOGAMI. 2021. https://online.plantvarieties.eu/publicConsultationDetails?registerId=20212288&denomination=ilvogami. 2 pages (Year: 2021).*

* cited by examiner

*Primary Examiner* — Karen M Redden
(74) *Attorney, Agent, or Firm* — Cassandra Bright

(57) ABSTRACT

A new and distinct cultivar of *Viburnum* plant named 'ILVOGAMI' is disclosed, characterized by a dense, columnar habit, abundant white flowers, and greyed-purple autumn foliage. The new variety is a *Viburnum*, normally produced as an outdoor garden or container plant.

2 Drawing Sheets

Latin name of the genus and species: *Viburnum plicatum.*
Variety denomination: 'ILVOGAMI'.

BACKGROUND OF THE INVENTION

The new *Viburnum* cultivar is a product of a planned breeding program conducted by the inventor in Melle, Belgium. The open-pollination resulting in this new variety was made during spring of 2009. The objective of the breeding program was to develop new cultivars of *Viburnum* for commercial horticultural purposes.

The seed parent of 'ILVOGAMI' is the unpatented *Viburnum plicatum* 'Watanabei'. The pollen parent is unidentified. The new variety was identified as a potentially interesting selection in 2012, at a research greenhouse in Melle, Belgium.

The first asexual propagation of 'ILVOGAMI' was carried out in 2019 by rooting stem cuttings at the same research greenhouse Melle, Belgium, and has been asexually reproduced repeatedly. 'ILVOGAMI' has been found to retain its distinctive characteristics through successive asexual propagations.

SUMMARY OF THE INVENTION

The cultivar 'ILVOGAMI' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ILVOGAMI' These characteristics in combination distinguish 'ILVOGAMI' as a new and distinct *Viburnum* cultivar:

1. Abundant white flowers.
2. Flowers from May to July, but can have a second flowering period in September.

3. Columnar shape.
4. Very dense, and densely branching.
5. Small leaves with a greyed-purple autumn coloration.

PARENT COMPARISON

Plants of the new cultivar 'ILVOGAMI' are similar to plants of the seed parent in most horticultural characteristics, however, plants of 'ILVOGAMI' differ in the following:

1. Plants of the new variety are more compact and dense than plants of the seed parent.
2. Plants of the new variety are about half as tall as plants of the seed parent.
3. Fall color of the new variety is greyed-purple; Fall foliage color of 'Watanabei' is orange-red with some dark purple.

The pollen parent is unidentified.

COMMERCIAL COMPARISON

Plants of the new cultivar 'ILVOGAMI' can be compared to the variety *Viburnum* 'ILVOMONO', U.S. Plant patent application Ser. No. 17/726,850. These varieties are similar in most horticultural characteristics; however, 'ILVOGAMI' differs in the following:

1. Flowers of the new variety are consistently white; flowers of this comparator begin pinkish and turn white.
2. Fall color of the new variety is greyed-purple; Fall foliage color of 'ILVOMONO' is greyed-red.

Plants of the new cultivar 'ILVOGAMI' can be compared to the variety *Viburnum* 'ILVOAWAI', U.S. Plant patent application Ser. No. 17/726,805. These varieties are similar in most horticultural characteristics; however, 'ILVOGAMI' differs in the following:

1. Flowers of the new variety are completely white; flowers of this comparator are pink and white.
2. Fall color of the new variety is greyed-purple; Fall foliage color of 'ILVOAWAI' is greyed-red.
3. Plants of 'ILVOGAMI' are both taller and wider than plants of 'ILVOAWAI'.

BRIEF DESCRIPTION OF THE PHOTOGRAPHS

This new *Viburnum* is illustrated by the accompanying photographs which show the plant's form, foliage and inflorescences. The colors shown are as true as can be reasonably obtained by conventional photographic procedures. Colors in the photographs may differ slightly from the color values cited in the detailed botanical description, which accurately describe the colors of the new *Viburnum* cultivar. Plants are approximately 4 to 5 years old.

DETAILED BOTANICAL DESCRIPTION

Figure 1:
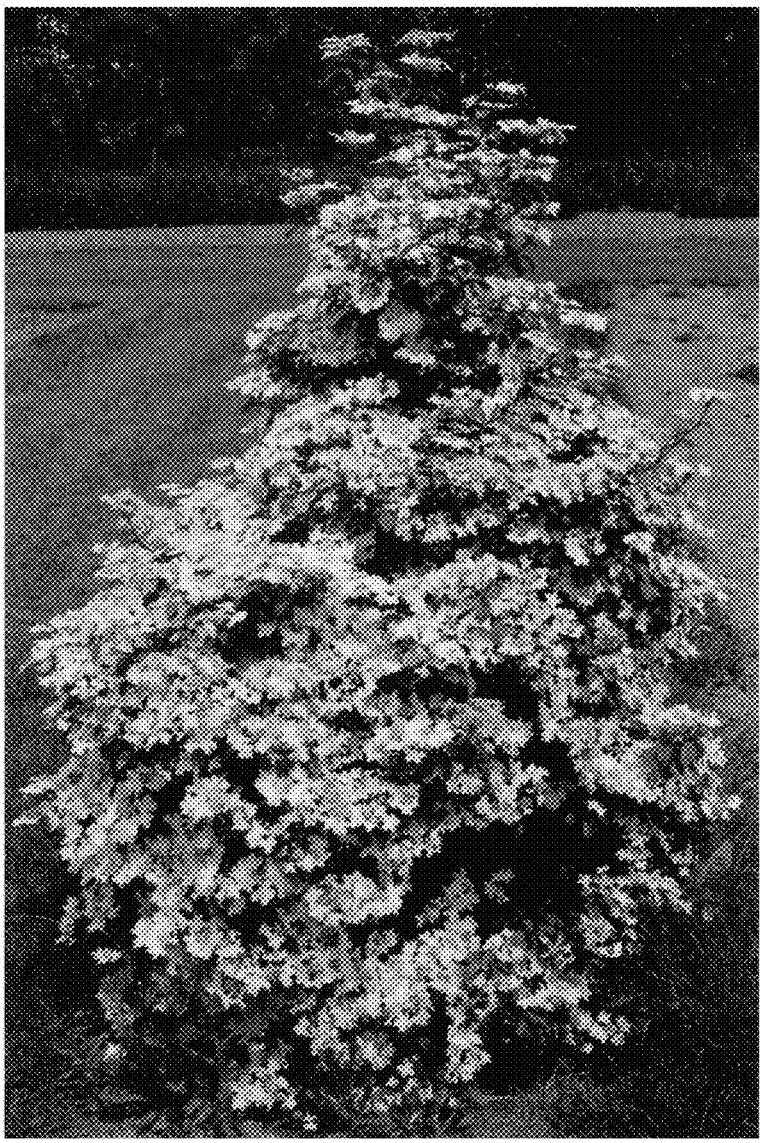
FIG. 1 is a color photograph of a field-grown plant of 'ILVOGAMI' in Grand Haven, Mich.
Figure 2:
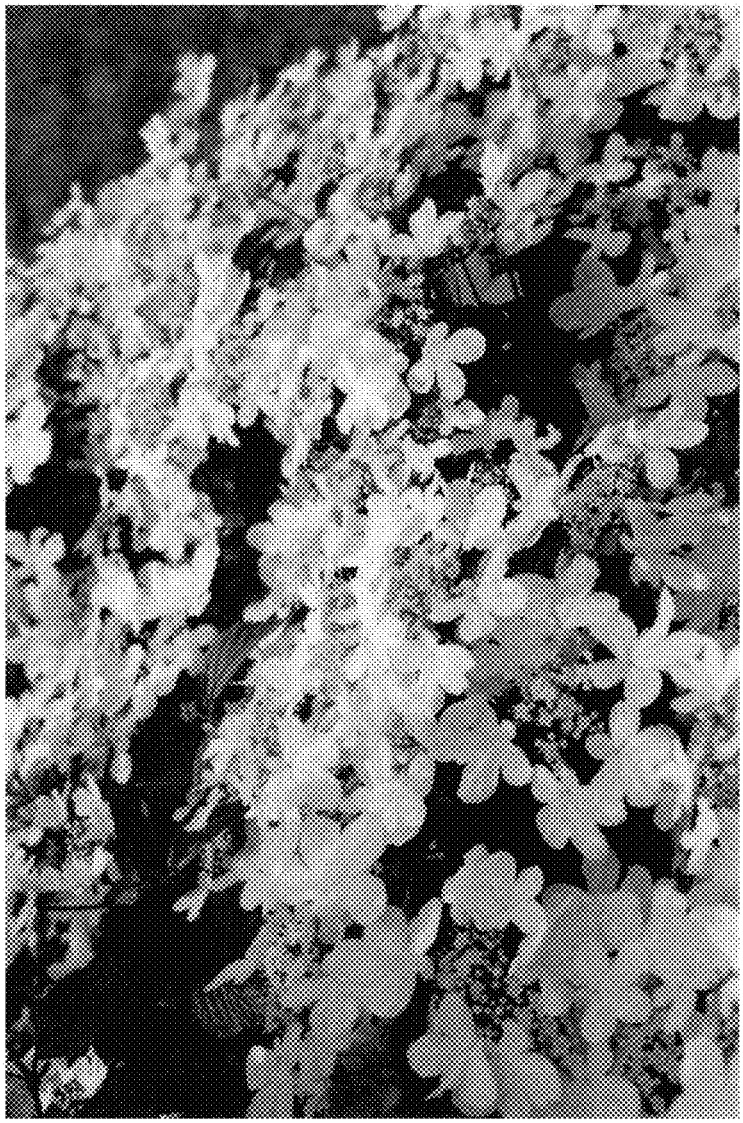
FIG. 2 is a color photograph showing inflorescences of 'ILVOGAMI' grown in Grand Haven, Mich.

The following is a detailed description of the botanical characteristics of the new and distinct *Viburnum* variety plant known by the denomination 'ILVOGAMI'. The detailed description was taken on a seven-year-old field-grown plant in Melle, Belgium in 2021. All colors cited herein refer to The Royal Horticultural Society Colour Chart (The Royal Horticultural Society (RHS), London, Sixth Edition). Where specific dimensions, sizes, colors, and other characteristics are given, it is to be understood that such characteristics are approximations or averages set forth as accurately as practicable.

Botanical classification: *Viburnum plicatum* 'ILVOGAMI'.

PROPAGATION

Typical method: Softwood cuttings.
Time to initiate rooting: 28 days at approximately 27° C.
Time to produce a rooted young plant: About 3 months at approximately 27° C.
Root description: Dense, free branching roots of moderate thickness. Colored yellow-white, not accurately measured with an RHS chart.

PLANT

Plant type: Perennial flowering shrub.
Plant description:
- *Growth habit.*—Upwards and slightly outwards.
- *Shape.*—Upright, columnar.
- *Height.*—170 cm.
- *Width.*—140 cm.
- *Growth rate.*—Good.
- *Vigor.*—Moderately vigorous.
- *Branching habit.*—Basal, freely branching.
- *Pinching required?.*—Not required, but if pinched, second flowering possible.

Stem:
- *Lateral branch length.*—Up to 70 cm.
- *Lateral branch diameter.*—0.5 to 0.8 cm.
- *Internode length.*—4 to 8 cm.
- *Stem texture.*—Smooth, glabrous.
- *Color.*—RHS Grey-Brown 199B.
- *Strength.*—Strong, erect stems.
- *Pubescence.*—None.

FOLIAGE

Leaf:
- *Persistence.*—Deciduous to semi-evergreen in warmer climates.
- *Arrangement.*—Opposite, single.
- *Shape.*—Elliptic.
- *Width.*—3 cm.
- *Length.*—6 cm.
- *Apex.*—Acuminate.
- *Base.*—Acute.
- *Venation.*—Reticulate.
- *Vein color.*—Near RHS Green 139A.
- *Margins.*—Dentate.
- *Pubescence.*—None.
- *Color.*—Immature: RHS Green 143A, upper and lower surfaces. Mature: RHS Green 141A and 141B, upper and lower surfaces; autumn coloration near Greyed-Purple 187B, upper and lower surfaces.

Petiole:
- *Length.*—1 to 1.5 cm.
- *Diameter.*—About 0.1 cm.
- *Color, upper side.*—RHS Red-Purple 60A-B to 59B.
- *Color, under side.*—RHS Red-Purple 60A-B to 59B.
- *Texture.*—Smooth, glabrous, both sides.

FLOWER

Description: Inflorescences on terminal ends of branches.
Inflorescence type: Compound umbel, lacecap.
Flowering season: May through July.
Longevity on plant: 3 months.
Persistent or self-cleaning?: Persistent.
Fragrance: None.
Flower:
- *Shape.*—Fertile flower Rotate, wheel-shaped. Sterile flower a single whorl of irregular petaloids.
- *Aspect.*—Upright, outward, both sterile and fertile flowers.

Bud:
- *Color, fertile flowers.*—When closed: RHS Yellow-Green 145B. Just before opening: RHS Yellow-White 158A-B. Color, sterile flowers: Near RHS Yellow-Green 144B.

Petals:
- *Number.*—4 to 5.
- *Arrangement.*—Rotated (both fertile and sterile flowers), arranged in a single whorl.
- *Fused?.*—Sterile flowers: Yes, fused at base. Fertile flowers: No.
- *Shape.*—Obovate-rounded.
- *Margin.*—Entire.
- *Apex.*—Obtuse.
- *Base.*—Rounded.
- *Texture.*—Smooth, both sides.
- *Color.*—Sterile flowers: RHS White 155A, upper and lower surfaces. Fertile flowers: RHS Yellow-White 158A and 158B, upper and lower surfaces.

Sepals: About 0.5 mm in size. Too minute for accurate measurement.
Peduncles:
- *Length.*—Average 1.5 cm.
- *Diameter.*—Average 1 mm.

*Color.*—Near RHS Yellow-Green 144B.
*Texture.*—Smooth, glabrous.
*Strength.*—Strong.

Pedicels:
*Length.*—Average 3 mm.
*Diameter.*—Average 1 mm.
*Color.*—Near RHS Yellow-Green 144B.
*Texture.*—Smooth, glabrous.
*Strength.*—Moderately strong.

REPRODUCTIVE ORGANS

Gynoecium:
*Pistil number.*—1.
*Stigma color.*—RHS White 155A.

Androecium:
*Stamen number.*—5.
*Filament length.*—About 0.5 cm.
*Filament color.*—RHS White 155A.
*Anther shape.*—Rounded, 2-lobed.
*Anther size.*—About 0.5 mm.
*Anther color.*—RHS Yellow 4C.
*Amount of pollen.*—Plentiful.
*Pollen color.*—RHS Yellow 4B.

OTHER CHARACTERISTICS

Fruit:
*Quantity.*—1 per flower.
*Length.*—About 4 mm.
*Diameter.*—About 3 mm.
*Shape.*—Elliptic.
*Color.*—Near RHS Greyed-Red 178A and 178B, turning near Black 203A when dessicated.
*Texture.*—Smooth.

Disease and insect resistance: No disease detected in 7 years.
Temperature tolerance: Tolerant from 40° C. to −10° C.

What is claimed is:

1. A new and distinct cultivar of *Viburnum* plant named 'ILVOGAMI' as herein illustrated and described.

* * * * *